(12) United States Patent
Pegard et al.

(10) Patent No.: US 9,873,657 B2
(45) Date of Patent: Jan. 23, 2018

(54) DERIVATIVES OF BENZYL BENZOATE

(71) Applicant: ROBERTET S.A., Grasse (FR)

(72) Inventors: Anthony Pegard, Grasse (FR); André Casazza, Grasse (FR); Raymond Kerverdo, St Vallier de Thiey (FR)

(73) Assignee: ROBERTET S.A., Grasse (FR)

( * ) Notice: Subject to any disclaimer, the term of this patent is extended or adjusted under 35 U.S.C. 154(b) by 0 days.

(21) Appl. No.: 15/129,501

(22) PCT Filed: Apr. 24, 2015

(86) PCT No.: PCT/FR2015/051115
§ 371 (c)(1),
(2) Date: Sep. 27, 2016

(87) PCT Pub. No.: WO2015/162392
PCT Pub. Date: Oct. 29, 2015

(65) Prior Publication Data
US 2017/0121270 A1    May 4, 2017

(30) Foreign Application Priority Data

Apr. 25, 2014    (FR) ...................... 14 53738

(51) Int. Cl.
*C07C 69/00* (2006.01)
*C07C 69/92* (2006.01)

(52) U.S. Cl.
CPC ................... *C07C 69/92* (2013.01)

(58) Field of Classification Search
CPC ............ C07C 69/92; A61K 8/37; A61Q 15/00
See application file for complete search history.

(56) References Cited

FOREIGN PATENT DOCUMENTS

| EP | 0169246 A1 | 1/1986 |
|----|------------|--------|
| JP | 60222446   | * 7/1985 |
| WO | 91/07165 A1 | 5/1991 |

OTHER PUBLICATIONS

Cavallito et al. (Chester J. Cavallito et al; "Synthesis of Phenolic Acid Esters. I. Depsides;" Journal of the American Chemical Society; 1943; vol. 65; pp. 2140-2142, as cited in IDS Filed Sep. 27, 2016).*
JP60222446 translation (Year: 1985).*
Jul. 14, 2015 International Search Report issued in International Patent Application No. PCT/FR2015/051115.
Chester J. Cavallito et al; "Synthesis of Phenolic Acid Esters. I. Depsides;" Journal of the American Chemical Society; 1943; vol. 65; pp. 2140-2142.
A Le Guen et al; "Synthesis and Properties of Flexible Poly(ether ketone) Backbones, Grafted With Stiff, Monodisperse Side Chains;" Macromolecules, American Chemical Society; 1998; vol. 31; No. 19; pp. 6559-6565.
Hao Lin et al: "Synthesis and antibacterial evaluation of anziaic acid and its analogues as topoisomerase I inhibitors;" MEDCHEMCOMM; 2013; vol. 4; No. 12; p. 1613-1618.

* cited by examiner

*Primary Examiner* — Yevgeny Valenrod
*Assistant Examiner* — Blaine G Doletski
(74) *Attorney, Agent, or Firm* — Oliff PLC

(57) ABSTRACT

A compound of the general formula (I)

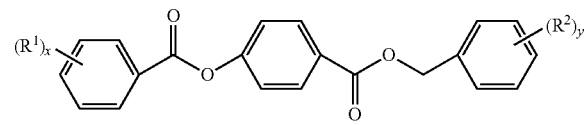

A cosmetic composition including such a compound and its use as a deodorant.

10 Claims, No Drawings

DERIVATIVES OF BENZYL BENZOATE

The present invention relates to new derivatives of benzyl benzoate and to the use of these derivatives for cosmetic applications, in particular as a deodorant.

The transpiration is a natural and necessary phenomenon which contributes in regulating the temperature of the body.

During the transpiration phases, the sudoriparous glands secrete sweat which contains essentially water, but also minerals and lactate.

In humans, there are two kinds of sudoriparous glands which differ by their functions and by the composition of the sweat that they excrete:

the <<eccrine>> sudoriparous glands; and the <<apocrine>> sudoriparous glands.

The eccrine sudoriparous glands are by far the most numerous and are located on almost the entire body but mainly on the palms of the hands, on the soles of the feet and on the forehead. Each of them is a simple, tubulous and spiral-shaped gland, the end of which, the glomerulus, is located in the thickness of the dermis or in the subcutaneous tissue.

The sweat secreted by the eccrine sudoriparous glands is 99% composed of water and electrolytes, in particular sodium chloride, and about 1% of organic compounds, in particular lactic acid. Although the sweat secreted by the eccrine sudoriparous glands has no odor in itself, it may, under some maceration conditions, be at the origin of bacterial infections or irritations.

The apocrine sudoriparous glands are located in particular under the armpits. They are bigger than the eccrine glands and their excretory duct opens into a hair follicle.

Besides the basic components identical to those of the sweat excreted by the eccrine glands, the sweat excreted by the apocrine glands also contains organic molecules (lipids and proteins) whose pheromones, which, once transformed by cutaneous bacteria, are at the origin of the odors called <<transpiration>> odors.

In order to prevent the apparition of these unpleasant odors, deodorant compositions, more commonly called <<deodorants>>, are in particular used. The deodorants may act in various manners:

by masking the unpleasant odors, for example thanks to perfume ingredients;

by absorbing sweat and by limiting the diffusion of the <<odorant>> molecules, for example thanks to a talc;

by acting directly on the bacteria which, when metabolizing the constituents of the apocrine sweat, release the odor attributed to transpiration.

For the preparation of effective deodorant compositions, it is therefore useful to identify compounds acting directly on the bacteria responsible for the odors called <<transpiration>> odors.

The international patent application WO 91/07165 describes the use of benzyl benzoate derivatives of the general formula

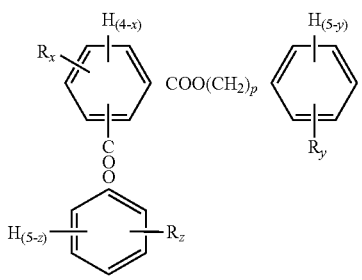

as antibacterial active agents allowing fighting the unpleasant odors.

In particular, this patent application describes the benzyl 4-benzoyloxybenzoate and its use for the preparation of deodorant compositions.

In *Synthesis and Properties of Flexible Poly(ether ketone) Backbones, Grafted with Stiff Monodisperse Sides Chaines*, Macromolecules, 1998, 31, 6559-6565, the authors describe a way of synthesis allowing preparing the benzyl-4-(benzoyloxy-1,4-benzoyloxy)benzoate. Nonetheless, no particular property is attributed to this compound.

These last years, besides the <<intrinsic>> effectiveness of the deodorant compositions, focus is also made on their durability, that is to say the duration over which the deodorant active agent is likely to effectively prevent the apparition of unpleasant odors.

In the context of the development of new deodorant compositions, it is therefore useful to identify the compounds allowing fighting effectively the apparition of the unpleasant odors during a prolonged duration in comparison with the already existing active agents.

Still, it has now been found out that new benzyl benzoate derivatives which, in a quite surprising manner, not only have an <<intrinsic>> effectiveness equivalent to those of the existing deodorant active agents, but also an improved duration of action in comparison with these same active agents.

Hence, the present invention relates to a compound of the general formula (I)

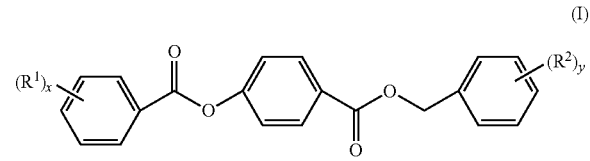

wherein:

x is an integer equal to 1, 2, 3, 4 or 5;

y is an integer equal to 0, 1, 2, 3, 4 or 5;

each substituent $R^1$ is chosen independently from the others as being a phenoxy group, a phenyl$C_1$-$C_6$-alkoxy group or a phenyl$C_1$-$C_6$-alkylcarbonyloxy group, each of these groups may possibly be substituted with one or several substituents chosen independently from each other as being a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group; and each substituent $R^2$ is chosen independently from the others as being a phenoxy group, a phenyl$C_1$-$C_6$-alkoxy group or a phenyl$C_1$-$C_6$-alkylcarbonyloxy group, each of these groups may possibly be substituted with one or several substituent(s) chosen independently from each other as being a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group with the exception of the benzyl-4-(benzoyloxy-1,4-benzoyloxy)benzoate.

The compounds according to the present invention have deodorant properties which are comparable to those of the existing active agents and present in addition a durable and prolonged effectiveness.

In the context of the present invention:
- by <<$C_1$-$C_6$-alkyl>>, is meant a saturated hydrocarbon chain, linear or branched, and including 1 to 6 atoms of carbon, in particular the methyl or ethyl group;
- by <<$C_1$-$C_6$-alkoxy>>, is meant a —O—($C_x$-$C_y$-alkyl) group, in particular the methoxy or ethoxy group;
- by <<phenyl$C_1$-$C_y$-alkoxy>>, is meant a —O—($C_x$-$C_y$-alkyl)Ph group, in particular the phenylmethoxy or phenylethoxy group;
- by <<phenyl$C_x$-$C_y$-alkylcarbonyloxy>>, is meant a —O—(C=O)—($C_x$-$C_y$-alkyl)Ph group, in particular the benzoyloxy group;
- the term <<alkyl>> as defined hereinabove keeps the same definition when it integrates the name of a group such as for example a hydroxyalkyl or alkylcarbonyloxy group;
- by <<deodorant>>, is meant any product or cosmetic composition intended to prevent, mask, eliminate or reduce the unpleasant body odors by acting in particular on the bacteria which, when metabolizing constituents of the apocrine sweat, release the odor that is attributed to transpiration;
- by <<deodorant treatment>>, is meant any cosmetic treatment comprising the application of one or several deodorant active agent(s) in order to prevent, mask, eliminate or reduce the apparition of the unpleasant body odors.

Preferably, the present invention relates to a compound of the general formula (I) as defined before wherein the following characteristics are chosen alone or in combination:
- x is an integer equal to 1, 2 or 3; still preferably, x is equal to 1 or 2; quite preferably, x is equal to 1;
- y is an integer equal to 0, 1 or 2; still preferably, y is equal to 0 or 1; quite preferably, y is equal to 0;
- each substituent $R^1$ is chosen independently from the others as being a phenoxy or benzoyloxy group, each of these groups may possibly be substituted with one or several substituents chosen independently from each other as being a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group; still preferably, each substituent $R^1$ is chosen independently from the others as being a phenoxy or benzoyloxy group, each of these groups may possibly be substituted with one or several hydroxyl group(s); quite preferably, each substituent $R^1$ is chosen independently from the others as being a phenoxy group possibly substituted with one or several hydroxyl group(s);
- each substituent $R^2$ is chosen independently from the others as being a phenoxy or benzoyloxy group, each of these groups may possibly be substituted with one or several substituent(s) chosen independently from each other as being a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group; still preferably, each substituent $R^2$ is chosen independently from the others as being a phenoxy or benzoyloxy group, each of these groups may possibly be substituted with one or several hydroxyl group(s); quite preferably, each substituent $R^2$ is chosen independently from the others as being a phenoxy group possibly substituted with one or several hydroxyl group(s).

Preferably, the present invention relates to a compound of the general formula (I-a)

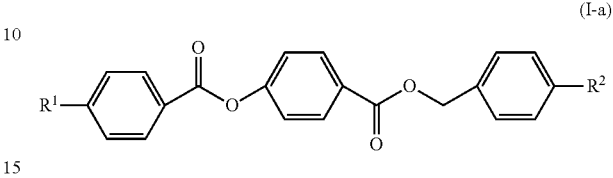

(I-a)

wherein $R^1$ and $R^2$ are as defined before.

Preferably, the present invention also relates to a compound of the general formula (I-b)

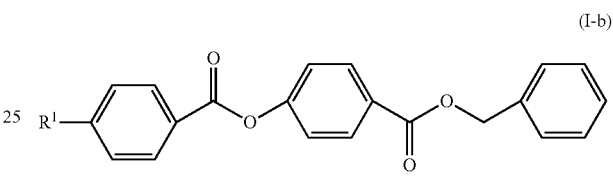

(I-b)

wherein $R^1$ is as defined before, with the exception of the benzyl-4-(benzoyloxy-1,4-benzoyloxy)benzoate.

The compounds of formula (I) may be prepared by any method known and conventionally used by those skilled in the art.

As example, the compounds of formula (I) according to the present invention may be prepared according to the following reaction scheme:

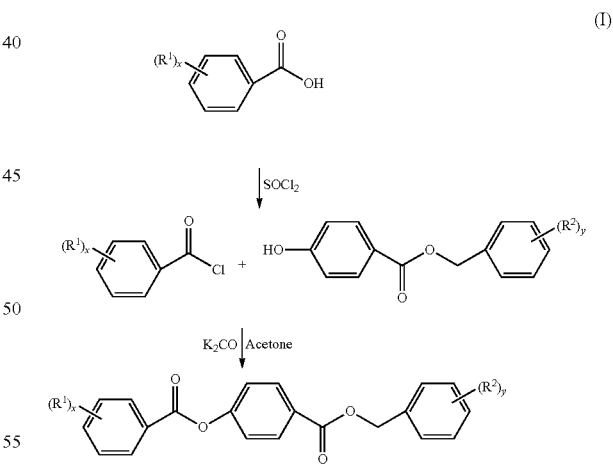

(I)

Hence, the compounds of formula (I) according to the present invention may be used in cosmetics for the deodorant treatment.

Hence, the present invention also relates to the cosmetic use of one or several compound(s) of formula (I) as defined before as a deodorant.

The present invention also relates to a cosmetic composition comprising (as an active principle) one or several compound(s) of formula (I) as defined before, as well as its use as a deodorant.

The cosmetic compositions according to the present invention may be formulated in any galenic form appropriate to their administration. Thus, the compositions according to the present invention may be formulated in the form of powders, cream, gel, lotion, milk, oil-in-water or water-in-oil emulsion, perfume, solution, ointment, spray, body oil, after-shave lotion, soap or stick.

The cosmetic compositions according to the present invention contain one or several compound(s) of formula (I) according to the present invention according to contents ranging from 0.005% to 25% by total weight of the composition, preferably from 0.01% to 15% by total weight of the composition, still preferably from 0.05% to 5% by total weight of the composition.

For the preparation of these cosmetic compositions, one or several compound(s) of formula (I) according to the present invention are mixed with excipients conventionally used in the cosmetic field.

The cosmetic compositions according to the present invention may be in the form of a perfume comprising one or several compound(s) of formula (I) according to the present invention. The thus prepared perfume may be in turn incorporated in another cosmetic composition.

The cosmetic compositions according to the present invention may be in the form of a cream in which one or several compound(s) of formula (I) according to the present invention are associated with excipients commonly used in cosmetology.

The cosmetic compositions according to the present invention may be in the form of gels in the appropriate excipients such as cellulose esters or other gelling agents, such as Carbopol, Sepinov (polyacrylate), guar gum, etc.

The cosmetic compositions according to the present invention may also be in the form of a lotion or a solution in which one or several compounds of formula (I) according to the present invention are in an encapsulated form.

The microspheres according to the invention may be constituted for example by fatty bodies, agar and water. One or several compound(s) of formula (I) according to the present invention may be incorporated in vectors of the type liposomes, glycospheres, cyclodextrins, in chylomicrons, macro-, micro-, nano-particles as well as macro-, micro- and nanocapsules and may also be absorbed on powdered organic polymers, talcs, bentonites and other mineral supports.

These emulsions have a good stability and may be preserved for the time necessary for their use at temperatures comprised between 0 and 50° C. without any sedimentation of the constituents or separation of the phases.

The cosmetic compositions according to the present invention may also contain additives or adjuvants common in cosmetology, such as for example antimicrobial agents or perfumes but also extraction or synthetic lipids, gelling and viscosifying polymers, surfactants and emulsifiers, hydro- or liposoluble active principles, plant extracts, tissue extracts, marine extracts, synthetic active agents.

The cosmetic compositions according to the present invention may also comprise other complementary active principles chosen for their action. When the compositions according to the present invention contain complementary active principles, these are generally present in the composition at a concentration which is high enough for them to exert their activity.

The cosmetic compositions according to the present invention are preferably used on a daily basis and applied once or several time(s) a day.

The present invention is illustrated in a non-limiting manner by the following examples.

EXAMPLE 1

Compounds According To The Invention

| Compound | M.P. (° C.) |
|---|---|
| Compound 1 (structure) | 112-120 |

EXAMPLE 2

Preparation Of The Benzyl[4-(4-Phenoxy)Benzoyloxy]Benzoate (Compound 1)

2-1 Preparation of the 4-phenoxybenzoyle chloride 10.7 g (50 mmol) of 4-phenoxybenzoic acid (CAS #2215-77-2; Aldrich 246182) are suspended in 75 ml of thionyl chloride (CAS #7719-09-7).

Heating is carried out progressively under magnetic stirring. The complete solubilization is obtained when the 60° C. temperature is reached. The set is maintained under gentle reflux for 45 minutes, then, evaporated to dryness in a Rotavapor.

The obtained yellow oil is the 4-phenoxy benzoyle chloride.

2.2 Preparation of the benzyl[4-(4-phenoxy)benzoyloxy]benzoate

In a 250 ml round-bottom flask, we place 11.4 g (50 mmol) of benzyl 4-hydroxybenzoate (CAS #94-18-8; Aldrich 300709), 55 ml of acetone (CAS #67-64-1) and 6.9 g (50 mmol) of anhydrous potassium carbonate (CAS #584-08-7).

The set is put under magnetic stirring and we rapidly add all the 4-phenoxybenzoyle chloride obtained at step 2.1 which has been dissolved beforehand in 100 ml of acetone.

After 2h15, stirring is made impossible by the formation of white-colored block.

The block is finely divided then diluted by additional 100 ml of acetone. The mixture has been poured into an excess of water. The solution is acidified by concentrated hydrochloric acid (CAS #7647-01-0) and extracted by 2×200 ml of dichloromethane.

The combined organic phases are evaporated to dryness resulting in 26 g of a white solid.

A filtration on 30 parts of silica (Kieselgel 60A, 70-230 mesh, Fluka) followed by an elution with dichloromethane then combination of the pure fractions (1) and concentration until the beginning of crystallization, dilution with pentane, spinning and washing with pentane, provides 15.85 g of white crystals (74.8% yield).

EXAMPLE 3

Deodorant Activity And Durability

Protocol

The test is carried out in vitro.

The compound 1 and the benzyl-4-benzoyloxybenzoate (reference compound described in the international patent application WO 91/07165) are both 10% diluted in benzylbenzoate, and incorporated in a specific culture medium at the moment of distribution in 50 ml vials.

The composition of the vials is characterized as follows:
Vial No. 1
  Brain Heart Infusion (medium)+0.5% Tween 40
  Compound 1 or benzyl-4-benzoyloxybenzoate—0.25%
  Enzyme (Lipozyme® CALB, Novozymes)—2%
  Bacteria (*Corynaebacterium xerosis*)—about 106 CFU/ml
Vial No. 2
  Brain Heart Infusion (medium)+0.5% Tween 40
  Compound 1 or benzyl-4-benzoyloxybenzoate—0.25%
  Bacteria (*Corynaebacterium xerosis*)—about 106 CFU/ml
Vial No. 3
  Brain Heart Infusion (medium)+0.5% Tween 40
  Compound 1 or benzyl-4-benzoyloxybenzoate—0.25%
  Enzyme (Lipozyme® CALB, Novozymes)—2%

Afterwards, the vials are incubated under stirring at 37° C. for 48 hours.

After 24 hours, a collection is performed, and 100 μl of a dilution to 1/1000th are spread out on gelose. Counting of the number of CFU (Colony Forming Units) is performed.

Results

It is the comparison of the ratios between the amount of CFU/ml at a time t for the product+enzyme and the product alone which allows assessing the inhibiting activity of the product.

The obtained results are reported in the Table hereinbelow.

| No. of the vial/Compound | Number of CFU/ml at t + 24 h | Number of CFU/ml at t + 48 h |
|---|---|---|
| Vial 1/Compound 1 | $10^7$ | 36000 |
| Vial 1/benzyl-4-benzoyloxybenzoate | $2.7 \times 10^6$ | $10^8$ |
| Vial 2/Compound 1 | $10^8$ | $3.2 \times 10^6$ |
| Vial 2/benzyl-4-benzoyloxybenzoate | $10^8$ | $10^9$ |
| Vial 3/Compound 1 | 0 | 0 |
| Vial 3/benzyl-4-benzoyloxybenzoate | 0 | 0 |

The obtained results clearly highlight:
a comparable deodorant activity of the compound and of the benzyl-4-benzoyloxybenzoate after 24 hours,
a deodorant activity of the compound 1 which is significantly higher relative to the benzyl-4-benzoyloxybenzoate after 48 hours.

The invention claimed is:

1. A compound of the general formula (I)

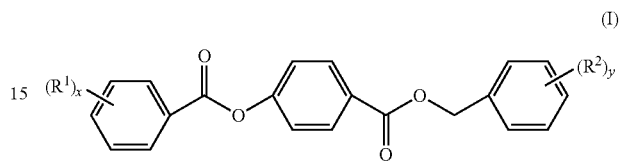

(I)

wherein:
  x is an integer equal to 1, 2, 3, 4 or 5;
  y is an integer equal to 0, 1, 2, 3, 4 or 5;
  each substituent $R^1$ is chosen independently from a phenoxy group, optionally substituted with one or several substituent(s) chosen independently from a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group; or a benzoyloxy group, substituted with one or several substituent(s) chosen independently from a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group; and
  each substituent $R^2$ is chosen independently from a phenoxy group, a phenyl$C_1$-$C_6$-alkoxy group or a phenyl$C_1$-$C_6$-alkylcarbonyloxy group, each of these groups optionally substituted with one or several substituents chosen independently from a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group.

2. The compound according to claim 1, wherein x is equal to 1, 2 or 3.

3. The compound according to claim 1, wherein y is equal to 0, 1 or 2.

4. The compound according to claim 1, wherein each substituent $R^1$ is chosen independently from a phenoxy optionally substituted with one or several hydroxyl groups; or benzoyloxy group, substituted with one or several hydroxyl groups.

5. The compound according to claim 1, wherein each substituent $R^2$ is chosen independently from a phenoxy or benzoyloxy group, each of these groups optionally substituted with one or several substituents chosen independently from a hydroxyl group, a $C_1$-$C_6$-alkyl group, a $C_1$-$C_6$-hydroxyalkyl group, a $C_1$-$C_6$-alkoxy group or a $C_1$-$C_6$-alkylcarbonyloxy group.

6. A compound of the general formula (I-a)

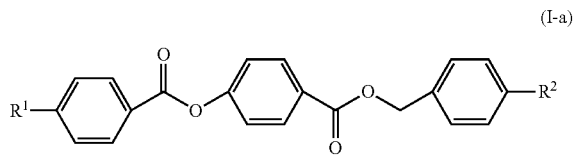

(I-a)

wherein $R^1$ and $R^2$ are as defined in claim 1.

7. A compound of the general formula (I-b)
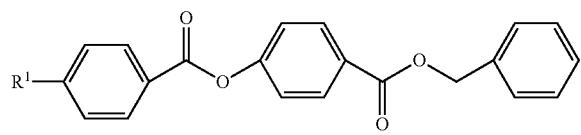
(I-b)
wherein R¹ is as defined in claim 1.
8. A method for preparing a compound according to claim 1 according to the following reaction scheme:
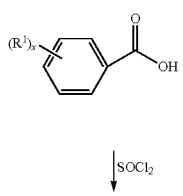
(I)
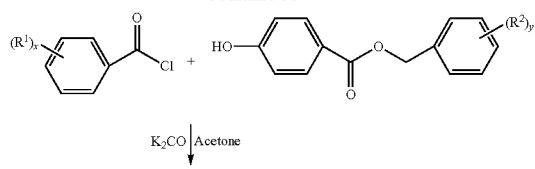
9. A cosmetic composition comprising a compound according to claim 1.
10. A deodorant comprising a composition according to claim 9.
* * * * *